United States Patent
Kugler et al.

(10) Patent No.: US 7,497,822 B1
(45) Date of Patent: Mar. 3, 2009

(54) STOMACH REDUCTION METHODS AND APPARATUS

(75) Inventors: Chad John Kugler, Andover, MN (US); Jerome Kent Grudem, Jr., Rogers, MN (US)

(73) Assignee: Torax Medical, Inc., Maple Grove, MN (US)

( * ) Notice: Subject to any disclaimer, the term of this patent is extended or adjusted under 35 U.S.C. 154(b) by 926 days.

(21) Appl. No.: 10/802,992

(22) Filed: Mar. 16, 2004

Related U.S. Application Data

(60) Provisional application No. 60/462,578, filed on Apr. 10, 2003.

(51) Int. Cl.
*A61F 2/00* (2006.01)
(52) U.S. Cl. .................................. 600/37; 606/151
(58) Field of Classification Search ............ 600/37; 606/151–157, 219, 139, 142; 128/897–898; 227/175.1
See application file for complete search history.

(56) References Cited

U.S. PATENT DOCUMENTS

| | | | |
|---|---|---|---|
| 4,154,226 A | 5/1979 | Hennig et al. | |
| 4,197,840 A | 4/1980 | Beck et al. | 128/76 |
| 4,271,827 A | 6/1981 | Angelchik | 128/1 R |
| 5,176,618 A | 1/1993 | Freedman | 600/12 |
| 5,234,447 A | 8/1993 | Kaster et al. | 606/153 |
| 5,234,448 A | 8/1993 | Wholey et al. | 606/153 |
| 5,387,235 A | 2/1995 | Chuter | 623/1 |
| 5,509,888 A | 4/1996 | Miller et al. | |
| 5,695,504 A | 12/1997 | Gifford, III et al. | 606/153 |
| 5,843,164 A | 12/1998 | Frantzen et al. | 623/1 |
| 5,876,448 A | 3/1999 | Thompson et al. | 623/12 |
| 5,957,949 A | 9/1999 | Leonhardt et al. | 606/194 |
| 6,056,744 A | 5/2000 | Edwards | 606/41 |
| 6,074,341 A | 6/2000 | Anderson et al. | |
| 6,136,006 A | 10/2000 | Johnson et al. | 606/108 |
| 6,146,416 A | 11/2000 | Andersen et al. | 623/1.15 |
| 6,302,917 B1 | 10/2001 | Dua et al. | 623/23.68 |
| 6,572,629 B2 * | 6/2003 | Kalloo et al. | 606/151 |
| 7,288,101 B2 * | 10/2007 | Deem et al. | 606/153 |
| 2002/0091295 A1 | 7/2002 | Wilk | 600/12 |
| 2003/0153806 A1 | 8/2003 | Miller | 600/30 |
| 2007/0208360 A1 * | 9/2007 | Demarais et al. | 606/153 |

FOREIGN PATENT DOCUMENTS

| | | |
|---|---|---|
| DE | 30 11 742 | 10/1981 |
| WO | WO 00/59398 | 10/2000 |
| WO | WO 01/47431 | 7/2001 |
| WO | WO 2004/004544 A2 | 1/2004 |

OTHER PUBLICATIONS

Shigley et al., *Mechanical Engineering Design*, Fifth Edition, 1989, McGraw-Hill, Inc., New York, pp. 58-60.

* cited by examiner

*Primary Examiner*—John P Lacyk
(74) *Attorney, Agent, or Firm*—Ropes & Gray LLP; Robert R. Jackson

(57) ABSTRACT

The effective volume of a patient's stomach cavity can be reduced by implanting at least two magnetic devices in the stomach at different locations on the stomach wall. The magnets cooperate with one another magnetically to change the effective volume of the stomach. For example, the magnets may magnetically attract one another to pull in portions of opposite side walls of the stomach. The magnetic devices may be implanted non-surgically (e.g., via one or more catheters introduced into the stomach cavity via the patient's mouth and esophagus). The magnets may be removable to reverse the treatment. Removal may be non-surgical.

15 Claims, 7 Drawing Sheets

STOMACH REDUCTION METHODS AND APPARATUS

This application claims the benefit of U.S. provisional patent application 60/462,578, filed Apr. 10, 2003, which is hereby incorporated by reference herein in its entirety.

BACKGROUND OF THE INVENTION

This invention relates to methods and apparatus for changing the geometry of a patient's stomach, and more particularly to methods and apparatus for reducing the size or volume of a patient's stomach, e.g., as a treatment for obesity.

The prevalence of obesity in modern human populations is a major problem. Obesity is a serious health risk, affecting an estimated 50 million people in the United States alone. In addition to becoming increasingly common, the age at which people are becoming obese is getting younger. Obesity can adversely affect an individual, both physically and mentally. Physically, obesity can cause heart disease, hypertension, and diabetes. Managing health problems related to obesity is estimated to cost the health care system in the United States $40,000,000,000 per year.

Weight reduction can be achieved either by an increase in caloric expenditure (e.g., by exercising) or by reducing caloric intake. Surgical methods have been developed for reducing stomach capacity and thus reducing food intake. Although these techniques can be effective, such relatively major surgery is not without risk.

In view of the foregoing, it would be desirable to develop less invasive stomach reduction procedures.

SUMMARY OF THE INVENTION

This and other objects of the invention are accomplished in accordance with the principles of the invention by providing procedures in which at least two objects that magnetically interact with one another are implanted in the stomach, preferably trans-orally. The two magnetic objects are implanted in the stomach at respective locations that can move relative to one another in response to magnetic interaction (force) between the magnetic objects. For example, the magnetic interaction (force) between the magnetic objects may induce the associated stomach wall portions to deflect toward one another, inwardly of the stomach cavity, thereby tending to reduce the volume of the cavity. This reduces the patient's desire to eat and thereby effectively treats the patient's obesity.

Further features of the invention, its nature and various advantages, will be more apparent from the accompanying drawings and the following detailed description.

DETAILED DESCRIPTION

Kugler et al. U.S. Pat. No. 7,445,010 shows implanting magnetic objects in a patient to treat various conditions such as GERD (gastro-esophageal reflux disease). Many of principles discussed in that reference (which is hereby incorporated by reference herein in its entirety, and which is sometimes referred to below as "the above-mentioned reference") are applicable to the present invention. It will not be necessary to expressly repeat herein everything from the above-mentioned reference that is applicable to the present invention. It will be sufficient to expressly provide herein a few representative examples of what can be done and what methods and apparatus can be used, and it will be understood that many other method and apparatus variations are possible, such as those that are shown and described in the above-mentioned reference. Also, some aspects and details of the construction and use of what is shown herein can be omitted from the present discussion because that information is readily found in the above-mentioned reference.

Another preliminary point is the following. For the most part this disclosure will discuss the use of magnetic objects that magnetically attract one another. This requires at least one magnetically active component (e.g., a magnetically polarized permanent magnet). The other magnetic object that magnetically cooperates with the first object can be either magnetically active and properly polarized for mutual magnetic attraction between the objects, or it can be magnetically passive (e.g., a body of ferromagnetic magnetic material that has no significant net external magnetic field in the absence of an adjacent magnetically active object). Possible variations on these arrangements include more than one magnetically passive object magnetically attracted to a magnetically active object, or two magnetically active objects that are polarized to magnetically repel (rather than attract) one another. A volume (e.g., of the stomach) can be reduced either by pulling two of its sides together using magnetic attraction, or by pushing two of its sides apart using magnetic repulsion, which causes other sides joining the first two sides to be pulled together and thereby reduces volume. Because of the ability to use either magnetically active or magnetically passive magnetic objects (as long as there is at least one magnetically active object in each group of magnetically interactive objects), the term "magnetic" will be used herein as a generic term for either magnetically active or magnetically passive components.

Figure 1:
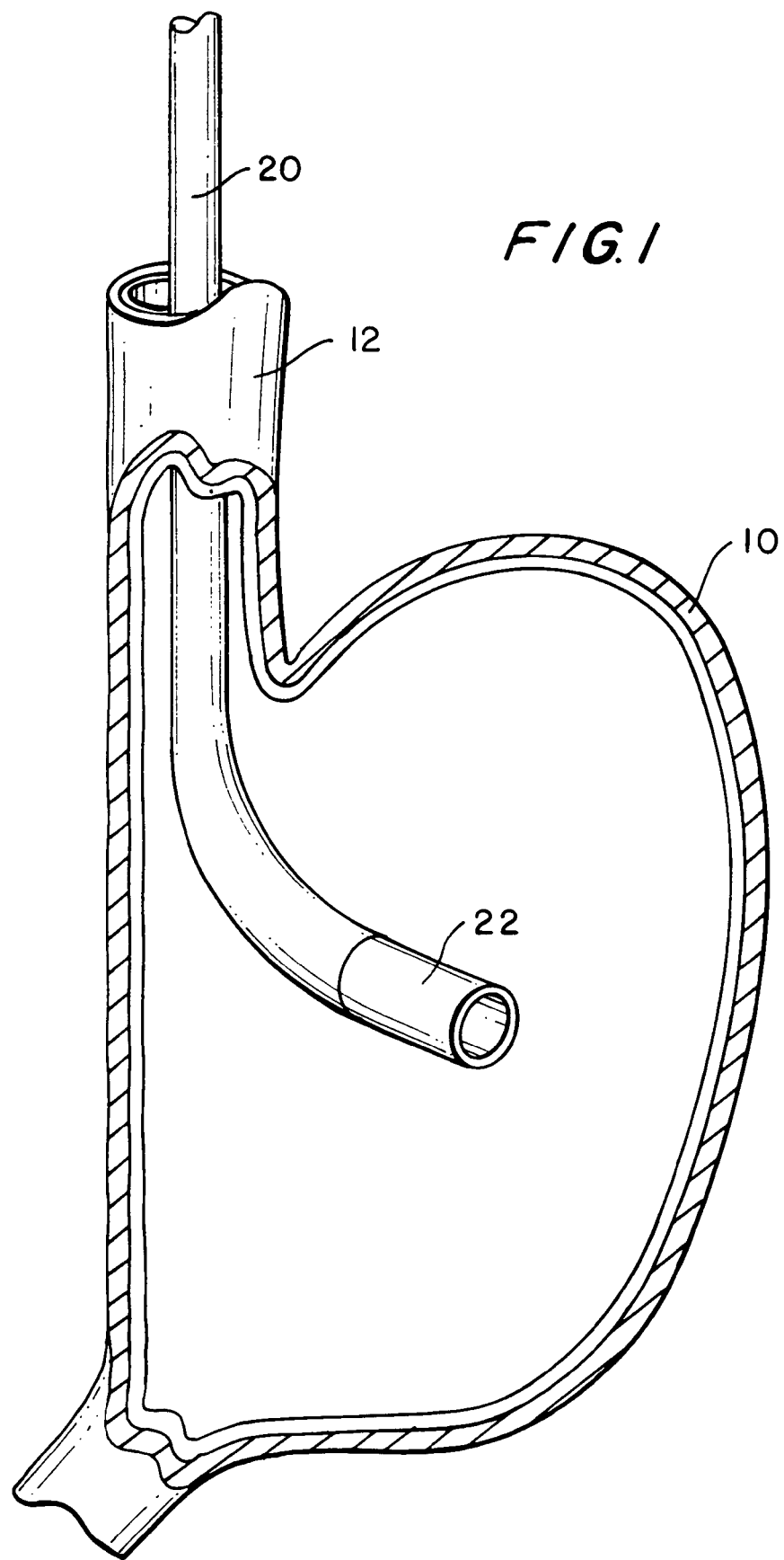
FIG. 1 is a simplified sectional view of a patient's stomach during part of an illustrative procedure in accordance with the invention.
Figure 2:
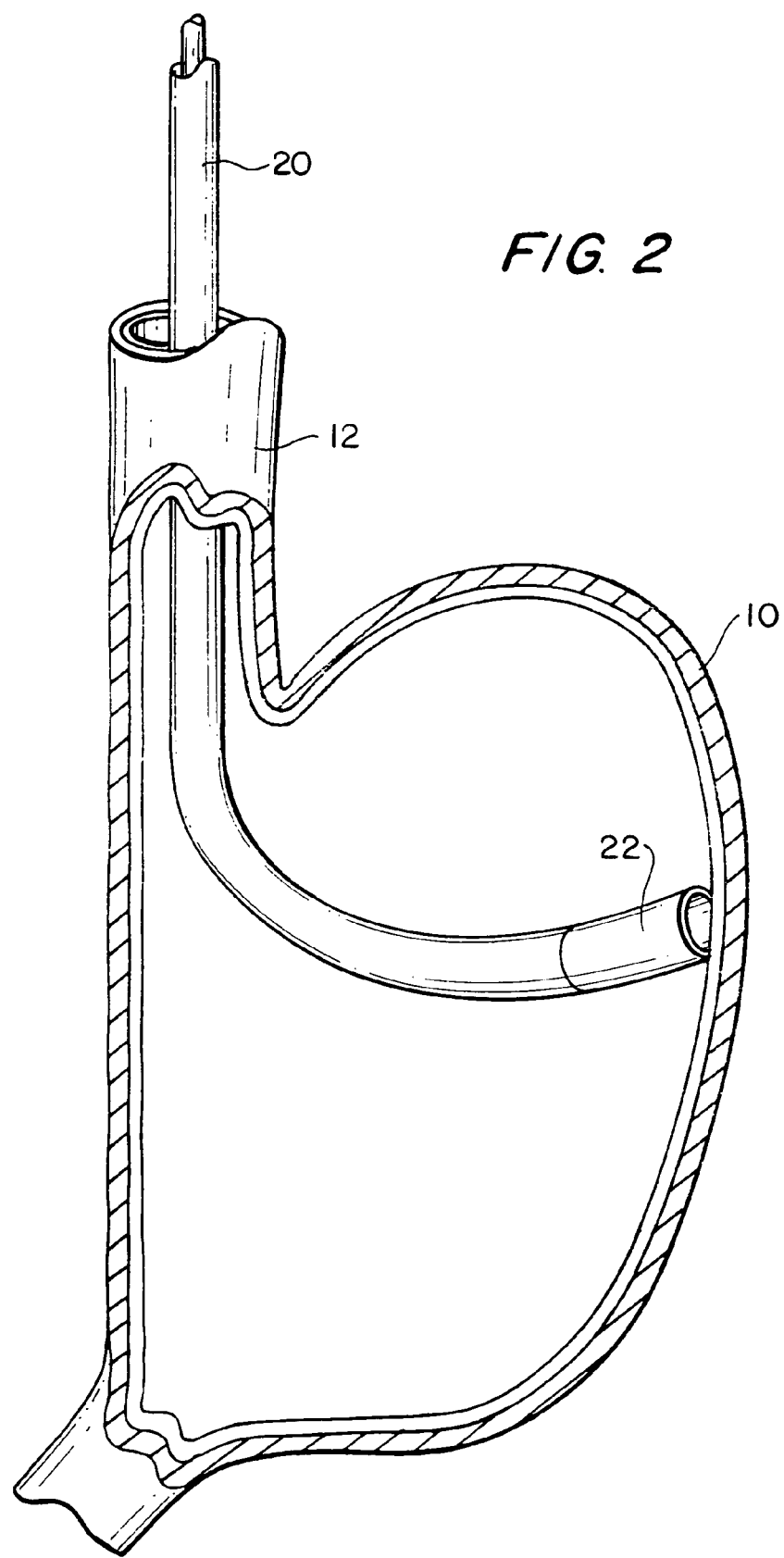
FIG. 2 is a view similar to FIG. 1 showing a later stage in the illustrative procedure.

In the illustrative embodiment shown in FIG. 1, endoscopic catheter 20 is introduced into a patient's stomach 10 through the patient's mouth and esophagus 12. The distal end 22 of catheter 20 is steered to a desired location on the wall of stomach 10 as shown, for example, in FIG. 2. Catheter 20 carries a magnetic object 30 in its distal end (see FIG. 3). Magnetic object 30 includes a magnetic body 32 (either magnetically active or magnetically passive as discussed above), a plurality of sharply pointed prongs 36 extending distally from body 32, and a structure 34 for attaching prongs 36 to body 32. Prongs 36 are resiliently biased to extend radially out from body 32. In the condition shown in FIG. 3, however, prongs 36 are deflected inwardly by being confined inside the distal portion 22 of catheter 20. In this condition the free end portions of prongs 36 are substantially parallel to one another, which means that they are substantially perpendicular to the wall of stomach 10 as the distal end 22 of catheter 20 approaches the stomach wall substantially perpendicular to that wall.

Figure 3:
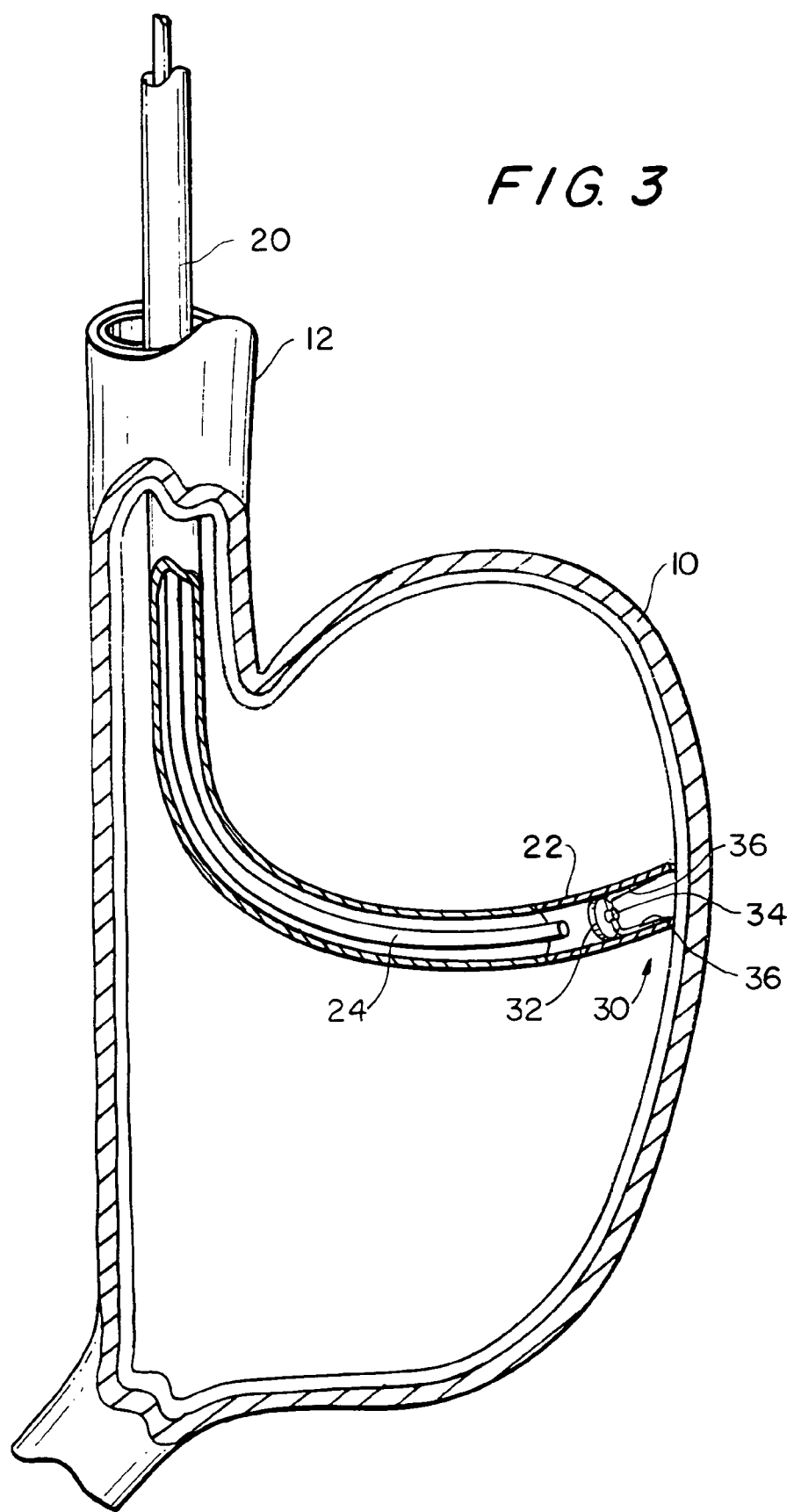
FIG. 3 is another view similar to FIG. 2 with more of the apparatus cut away to reveal its internal construction.
Figure 4A:
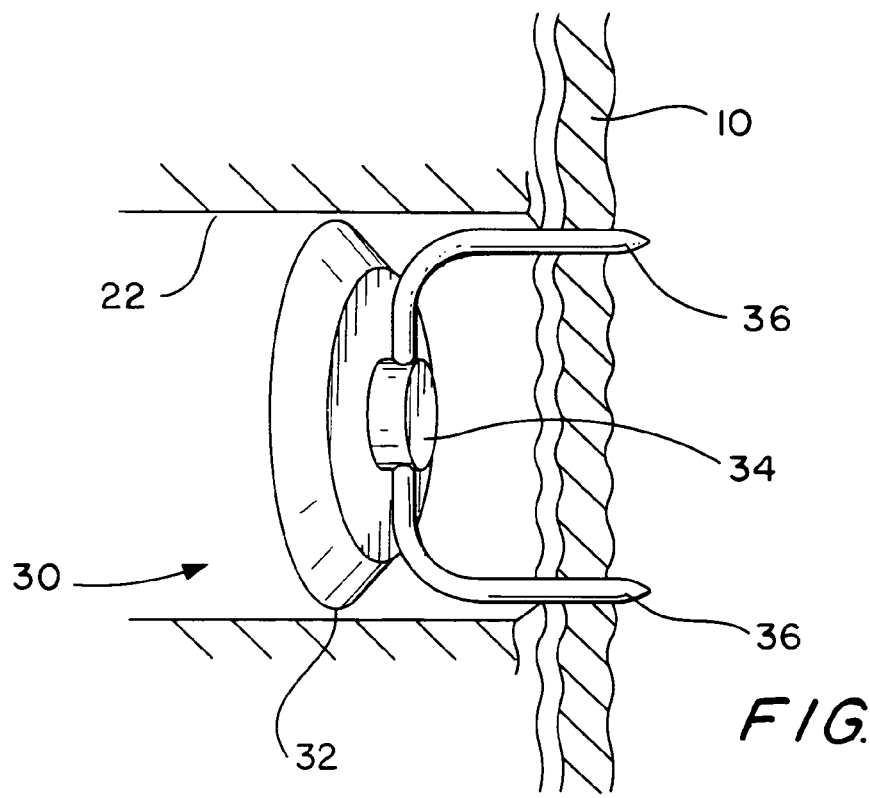
FIG. 4A is a simplified sectional view showing an illustrative magnetic object being implanted in the wall of the stomach in accordance with the invention.
Figure 4B:
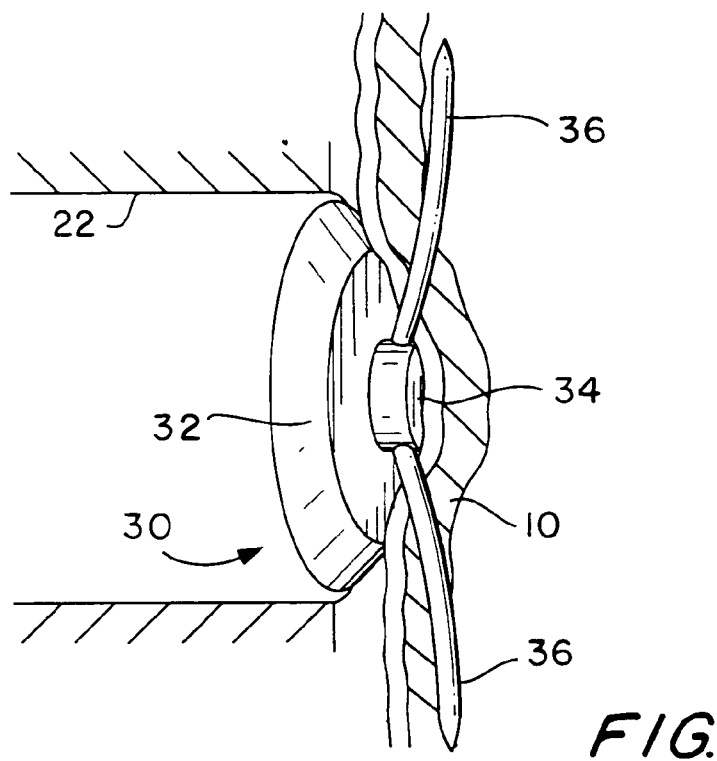
FIG. 4B is another view similar to FIG. 4A showing a later stage of what is shown in FIG. 4A.

When the distal end 22 of catheter 20 is against the wall of stomach 10 at the desired location as shown in FIG. 3, magnetic object 30 is pushed out the distal end of the catheter into the wall of the stomach by distal motion of pusher 24 relative to the remainder of catheter 20. FIGS. 4A and 4B show the progress of magnetic object 30 as it is thus pushed out of catheter 20 and becomes implanted in the tissue of the stomach wall. Initially (FIG. 4A) prongs 36 are forced into stomach wall tissue 10 substantially parallel to one another, which facilitates entry of the prongs into the tissue. As prongs 36 leave the distal portion 22 of the catheter and are therefore no longer constrained by the catheter to remain substantially parallel to one another, prongs 36 resiliently flare out in or beyond tissue 10 so that they become more nearly radial of magnetic body 32 (see FIG. 4B). In this spread-apart condition (FIG. 4B), prongs 36 hold magnetic object 30 securely to the wall of stomach 10.

To facilitate the above-described implanting of magnetic object 30, tension may be placed on the stomach wall at the site of the implant. This may be done prior to and during the implantation to ensure good engagement of retention fingers 36 into the stomach wall tissue. Such tension can be achieved by pulling vacuum on the tissue via catheter 20, or by mechanically expanding the stomach at the implant site.

Figure 5A:
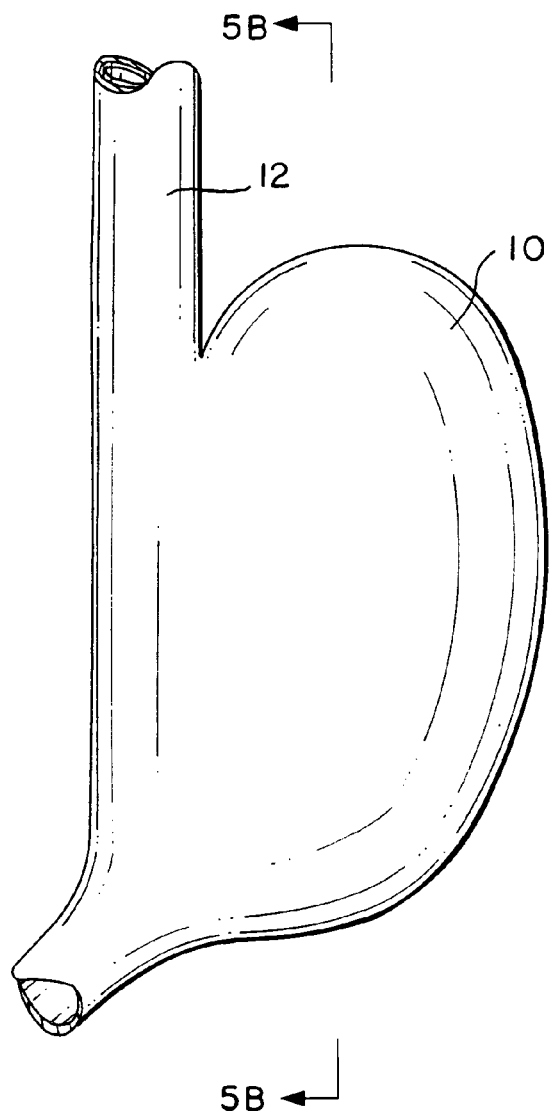
FIG. 5A is a simplified external view of a stomach that has been treated in accordance with the invention.
Figure 5B:
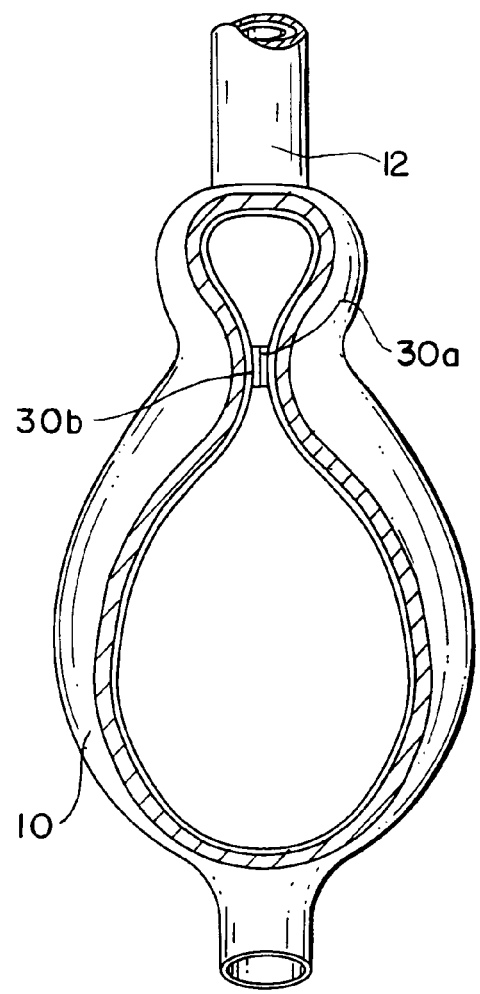
FIG. 5B is a simplified sectional view taken along the line 5B-5B in FIG. 5A.

After magnetic object 30 has been implanted in the stomach as described above, a second magnetic object (which can be generally similar to object 30) is similarly implanted in stomach 10 at a location which is different from the location of the first magnetic object but which places the second object where it can magnetically interact with the first to produce a reduction in the volume of stomach 10. For example, FIGS. 5A and 5B show two magnetic objects 30a and 30b implanted opposite one another on opposite sides of stomach 10. In this embodiment magnetic objects 30a and 30b magnetically attract one another. Accordingly, when stomach 10 is relatively empty, magnetic objects 30a and 30b magnetically attach to one another. This attachments "pins" the opposing stomach walls together, thereby reducing the effective volume and expandability of stomach 10.

Figure 6A:
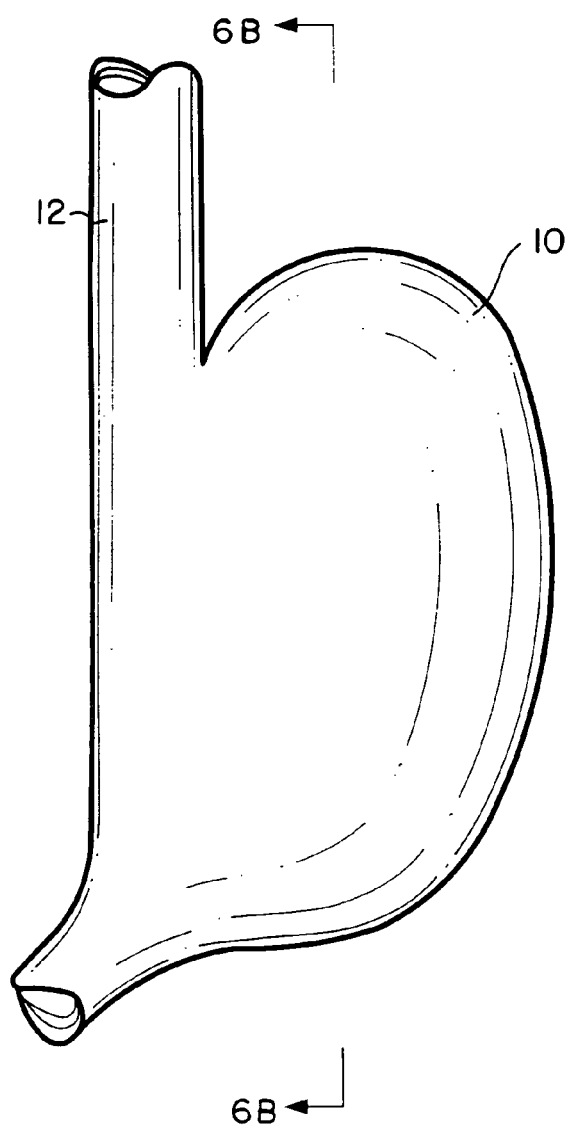
FIG. 6A is another view similar to FIG. 5A showing a stomach that has been alternatively or additionally treated in accordance with the invention.
Figure 6B:
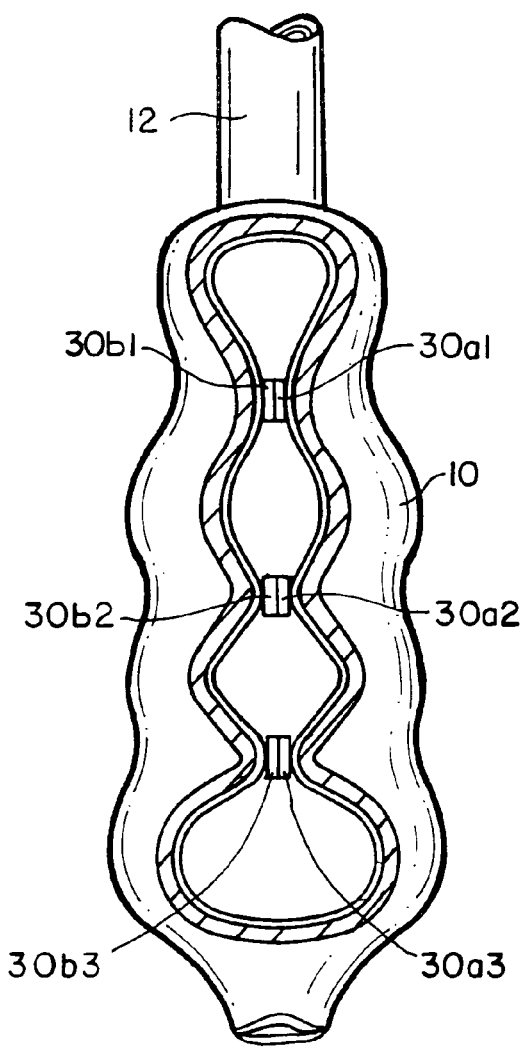
FIG. 6B is a simplified sectional view taken along the line 6B-6B in FIG. 6A.

Multiple pairs of magnets 30 may be implanted to achieve a desired change in the volume or geometry of the stomach cavity. FIGS. 6A and 6B, for example, show implanting three pairs of magnets 30a/b1, 30a/b2, and 30a/b3.

An illustrative use of the invention is to isolate the fundus area from the rest of the stomach to limit its ability to expand if the patient attempts to over-eat.

Figure 7:
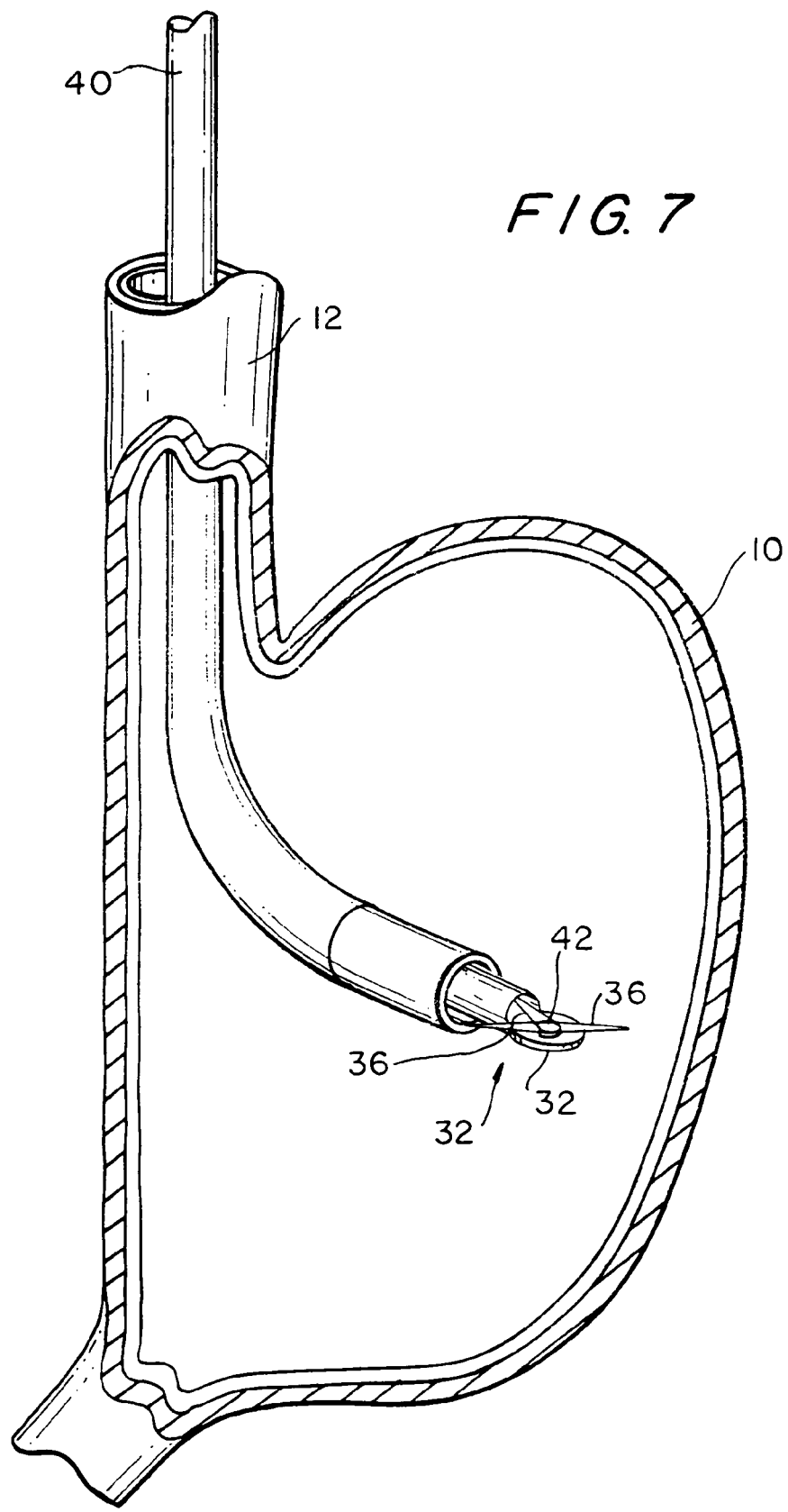
FIG. 7 is generally similar to FIG. 1 but shows illustrative reversal of treatment in accordance with the invention.

Although prongs 36 hold each magnetic object 30 securely in stomach 10 as described above, a magnetic object 30 can be removed from the stomach if desired. For example, FIG. 7 shows that another catheter 40 can be inserted into stomach 10 via the patient's mouth and esophagus 12 and steered to a magnetic object to be removed. A loop 42 of a strand material (e.g., metal wire or dacron cord) is placed around object 30 behind magnetic body 32 but in front of prongs 36. With loop 42 tightened around object 30, catheter 40 can be retracted to pull object 30 free from the stomach wall. If desired (e.g., in the interest of atraumatic removal of object 30 through esophagus 12, etc.) object 30 can be pulled completely inside the protective distal end 44 of catheter 40 before that end of catheter 40 is pulled back into esophagus 12 and out of the patient. An illustrative use of magnet removal as shown in FIG. 7 is to remove one or more magnets 30 after the patient has achieved a desired amount of weight reduction.

Although the illustrative embodiment expressly described above includes introducing magnetic objects 30 trans-orally, it will be understood that other methods (e.g., other endoscopic methods) may be used instead, if desired.

To briefly recapitulate, at least part of the scope of this disclosure is to describe methods and apparatus for modifying the geometry and/or the volume of the stomach by using one or more magnet pairs to pin the inner opposing walls of the stomach together magnetically. Because the magnets can be delivered from a catheter, trans-orally into the stomach cavity, procedural invasiveness is dramatically reduced relative to the known surgical techniques for stomach reduction. An additional benefit of the present magnetic reduction method is that the magnets can be removed by non-invasive or minimally invasive techniques similar to those by which the magnets are implanted. The procedure is therefore reversible. The number, size, and locations of the magnets within the stomach can be varied to achieve a specific result.

It is additionally mentioned here that a U.S. provisional patent application (Kugler et al. application 60/547,200, filed Feb. 23, 2004) has been filed on medicating implants of the general type shown herein. The teachings contained in that provisional patent application (which is hereby incorporated by reference herein in its entirety) can be applied in the context of this invention if desired.

It will be understood that the foregoing is only illustrative of the principles of the invention, and that various modifications can be made by those skilled in the art without departing from the scope and spirit of the invention. For example, other constructions of magnetic devices 30 are possible, and some such other constructions are shown in the above-mentioned reference (and in the provisional application on medicated implants that is also mentioned above).

The invention claimed is:

1. A method of reducing the effective volume of a patient's stomach cavity comprising:

implanting a first magnetic device on an inner surface of the stomach cavity at a first location; and implanting a second magnetic device on an inner surface of the stomach cavity at a second location, the first and second locations being selected to be across the stomach cavity from one another but to be movable toward one another across the stomach cavity to allow the first and second magnetic devices to contact one another as a result of magnetic attraction between the first and second magnetic devices.

2. The method defined in claim 1 wherein the implanting steps are performed from inside the stomach cavity.

3. The method defined in claim 2 wherein the implanting steps are performed trans-orally.

4. The method defined in claim 1 wherein at least one of the implanting steps is reversible by removing at least one of the magnetic devices.

5. The method defined in claim 4 wherein the removing is performed from inside the stomach cavity.

6. The method defined in claim 5 wherein the removing is performed trans-orally.

7. Apparatus for reducing the effective volume of a patient's stomach cavity comprising:

first and second magnetic implants at respective first and second stomach wall locations that are across the stomach cavity from one another but that are movable toward one another across the stomach cavity to allow the first and second magnetic implants to contact one another as a result of magnetic attraction between the first and second magnetic implants, resulting in an application of force to the stomach wall locations.

8. The apparatus defined in claim 7 wherein the force is directed toward the interior of the stomach cavity.

9. The apparatus defined in claim 7 wherein the force tends to produce deflection of at least one of the stomach wall locations.

10. The apparatus defined in claim 9 wherein the deflection is inwardly of the stomach cavity.

11. The apparatus defined in claim 7 wherein each of the magnetic implants is configured for implanting from inside the stomach cavity.

12. The apparatus defined in claim 11 wherein each of the magnetic implants is configured for implanting via catheter-like instrumentation inserted into the stomach cavity.

13. The apparatus defined in claim 12 wherein the catheter-like instrumentation is trans-oral.

14. The apparatus defined in claim 11 wherein at least one of the magnetic implants is configured for removal via catheter-like instrumentation inserted into the stomach cavity.

15. The apparatus defined in claim 14 wherein the catheter-like instrumentation is trans-oral.

* * * * *